(12) United States Patent
Doshi et al.

(10) Patent No.: US 8,778,379 B2
(45) Date of Patent: Jul. 15, 2014

(54) INSERTABLE MEDICAL DEVICES WITH A POROUS BED FOR DELIVERING NANO-CARRIERS TO A TARGET SITE AND METHODS OF PREPARING THE SAME

(75) Inventors: Manish Doshi, Surat (IN); Divyesh Sherdiwala, Surat (IN); Prakash Sojitra, Surat (IN)

(73) Assignee: Concept Medical Research Private Ltd, Surat (IN)

( * ) Notice: Subject to any disclaimer, the term of this patent is extended or adjusted under 35 U.S.C. 154(b) by 0 days.

(21) Appl. No.: 13/063,200

(22) PCT Filed: Jan. 19, 2011

(86) PCT No.: PCT/IN2011/000040
§ 371 (c)(1),
(2), (4) Date: Mar. 9, 2011

(87) PCT Pub. No.: WO2011/089624
PCT Pub. Date: Jul. 28, 2011

(65) Prior Publication Data
US 2012/0315300 A1  Dec. 13, 2012

(30) Foreign Application Priority Data
Jan. 22, 2010 (IN) .......................... 178/MUM/2010

(51) Int. Cl.
*A61F 2/00* (2006.01)
(52) U.S. Cl.
USPC ........................................................ 424/423
(58) Field of Classification Search
None
See application file for complete search history.

(56) References Cited

U.S. PATENT DOCUMENTS

| | | | |
|---|---|---|---|
| 6,117,455 A | * | 9/2000 | Takada et al. ................. 424/501 |
| 6,387,453 B1 | | 5/2002 | Brinker et al. |
| 2006/0193890 A1 | * | 8/2006 | Owens et al. ................. 424/423 |

FOREIGN PATENT DOCUMENTS

| | | |
|---|---|---|
| CN | 1806857 | 7/2006 |
| CN | 101437467 | 5/2009 |
| CN | 101448534 | 6/2009 |

OTHER PUBLICATIONS

International Search Report dated Oct. 27, 2011, PCT Application No. PCT/IN2011/000040, 6 pages.

* cited by examiner

*Primary Examiner* — Brian Gulledge
(74) *Attorney, Agent, or Firm* — Timberline Patent Law Group PLLC

(57) ABSTRACT

The invention discloses a method of coating a medical device. The method includes applying a coating composition on the medical device to form a layer on the medical device. The coating composition includes one or more of one or more biological agents and heparin dissolved in a mixture of a first solvent and a second solvent. The first solvent and the second solvent have different evaporation temperatures. Subsequently, at least a part of one of the first solvent and the second solvent present in the coating composition is evaporated to create a plurality of pores in the layer. Thereafter, one or more drugs are deposited in the plurality of pores. When the medical device is positioned and expanded at a target site, the one or more drugs are released from the plurality of pores.

14 Claims, 2 Drawing Sheets

US 8,778,379 B2

INSERTABLE MEDICAL DEVICES WITH A POROUS BED FOR DELIVERING NANO-CARRIERS TO A TARGET SITE AND METHODS OF PREPARING THE SAME

RELATED APPLICATIONS

This application claims the benefit of priority to International PCT Application PCT/IN2011/000040 filed Jan. 19, 2011 and incorporated herein by reference, which in turn claims the benefit of priority to India Patent Application No. 178/MUM/2010 filed Jan. 22, 2010 and incorporated herein by reference.

FIELD OF THE INVENTION

The invention generally relates to a method of coating a medical device. More specifically, the invention relates to a method of preparing a porous layer on surface of a medical device and the medical device prepared using the method.

BACKGROUND OF THE INVENTION

Currently, medical devices that are used for delivering nano/micro-particles of the drugs to a target site in a blood vessel include the Drug Eluting Balloons (DEBs), the Drug Eluting Stents (DESs) and the like. Generally, polymers are used along with the nano/micro-particles of the drugs for loading the nano/micro-particles of the drugs on the surfaces of the medical devices. However, the use of polymers is associated with several side effects. For example, the drug delivering medical devices with nano/micro-particles of the drug encapsulated with a polymer may produce inflammation at the target site. Further, because of improper degradation of the polymer, the drug may be delivered in an uncontrolled manner. In addition, a semi-degradation of polymers may result in the "knife effect" and the "edge effect".

Usually while using the DESs, both the inner surface and the outer surface of the stent are coated with the drugs and the polymers. As the inner surface of the DESs carries the drug, the DESs are associated with delayed healing and improper healing of the affected area. The delayed healing and the improper healing may result in sub-acute thrombus formation and late thrombus formation. Additionally, most of the drugs that are administered to the blood vessel using the DEBs and the DESs have a lipophilicity insufficiency in achieving an in-tissue diffusion of the drugs. As a result, the existing DEBs and DESs are associated with the phenomenon of focal restenosis.

In order to avoid the side effects associated with the polymers, few non-polymeric approaches are also used in the art for loading the nano/micro-particles of the drugs on the surface of the DEBs and the DESs. However, the non-polymeric approaches are generally based on surface modification of the DEBs and the DESs. The surface modification approaches may not guarantee uniform distribution of the nano/micro-particles of the drugs across the affected area. This may further lead to improper healing and delayed healing of the affected area. Further, the non-polymeric approaches can be used only for loading and delivering certain highly lipophilic drugs like paclitaxel. Whereas, the relatively low lipophilic drugs like sirolimus may not be successfully loaded on the surface of the medical device and delivered there from using the non-polymeric approaches.

Therefore, there is a need in the art for an improved method of loading the drugs on the surface of insertable and/or implantable medical devices without using polymers and without modifying the surface of the insertable and/or implantable medical devices.

DETAILED DESCRIPTION OF THE INVENTION

Before describing in detail embodiments that are in accordance with the invention, it should be observed that the embodiments reside primarily in combinations of method steps of coating a medical device and components of the medical device. Accordingly, the method steps and the components have been described to include only those specific details that are pertinent to understanding the embodiments of the invention so as not to obscure the disclosure with details that will be readily apparent to those of ordinary skill in the art having the benefit of the description herein.

In this document, the terms "comprises," "comprising," or any other variation thereof, are intended to cover a non-exclusive inclusion, such that a process, method, article, or device that comprises a list of elements does not include only those elements but may include other elements not expressly listed or inherent to such process, method, article, or device. An element preceded by "comprises . . . a" does not, without more constraints, preclude the existence of additional identical elements in the process, method, article, or apparatus that comprises the element.

Further, before describing in detail embodiments that are in accordance with the invention, it should be observed that all the scientific and technical terms used in for describing the invention have same meanings as would be understood by a person skilled in the art.

Pursuant to various embodiments, the invention discloses a method of coating a medical device. The medical device includes one or more of, but are not limited to, an insertable medical device and an implantable medical device. Examples of the medical device include, but are not limited to, a stent, a balloon, a pre-crimped stent, a catheter and an implant. Alternatively, the medical device may be any other medical device that may be inserted or implanted into a body lumen without departing from the scope of the invention.

Figure 1:
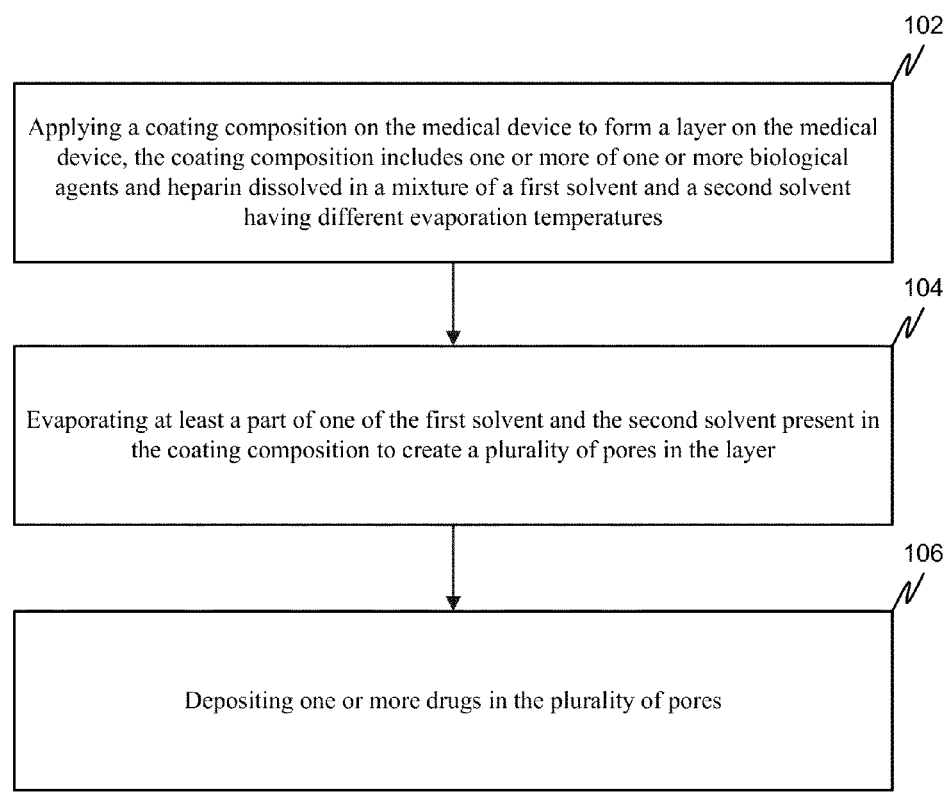
FIG. 1 illustrates a flow chart of a method of coating a medical device in accordance with an embodiment.

FIG. 1 illustrates a flow chart of a method of coating a medical device in accordance with an embodiment. As illustrated in FIG. 1, the method includes applying a coating composition on the medical device to form a layer on the medical device at step 102. The coating composition may be applied on the medical device using methods and techniques known in the art. The coating composition includes one or more of one or more biological agents and heparin dissolved in a mixture of two or more solvents with different evaporation temperatures. The one or more biological agents include, one or more of, but are not limited to, a drug carrier, a blood component, a phospholipid, solid lipid nano-particles, a lipoid, a vitamin and a sugar molecule.

Examples of the one or more biological agents include, but are not limited to, a steroid, an estradiol, an esterified fatty acid, a non-esterified fatty acid, glucose, an inositol, L-lactate, a lipoprotein, a carbohydrates, tricalcium phosphate, precipitated calcium phosphate, a substance derived from one of human, egg and soybean, phospholipon 80H, phospholipon 90H, Lipoid S75, Lipoid E80, Intralipid 20, Lipoid EPC, Lipoid E75, a lipid obtained from one of egg and soya, phosphatidylcholine, phosphatidylglycerol, phosphatidylinositol, phosphatidylserine, phosphatidic acid, cardiolipin, and phosphatidylethanolamine. In an embodiment, the one or more biological agents are one of Lipoid E80 and tricalcium phosphate.

In accordance with various embodiments, the one or more biological agents are dissolved in a mixture of two or more solvents with different evaporation temperatures. For example, the one or more biological agents may be dissolved in a first solvent and a second solvent having a first evaporation temperature and a second evaporation temperature respectively. In an embodiment, the one or more biological agents may be dissolved in a first solvent and a second solvent having a first evaporation rate and a second evaporation rate respectively. In accordance with various embodiments, the first evaporation temperature and the first evaporation rate are different from the second evaporation temperature and the second evaporation rate respectively. For example, the first solvent may be a low-evaporating or a low-boiling solvent as compared to the second solvent.

The one or more solvents include solvents in which the one or more biological agents and the one or more drugs are soluble without alteration of therapeutic effects of the one or more drugs and the one or more biological agents. The one or more solvents include, one or more of, but are not limited to, an alcohol, a chlorine substituted methane, a chlorine substituted ethane, an ether, an ester. Examples of the one or more solvents include, but are not limited to, methanol, ethanol, iso-propyl alcohol, trichloromethane, tetrachloromethane, tetrachloroethane, trichloroethane, Dimethyl sulfoxide (DMSO), tetrahydrofuran, dichloromethane, chloroform, n-propanol, dimethylformamide, dimethylacetamide. In some embodiments, the one or more solvents include alcohols (e.g., methanol, ethanol, 1,3-propanol, 1,4-butanol), heptane, hexane, pentane, cyclohexanone, trichloroethane, acetone, tetrahydrofuran (THF), dimethyl acetamide (DMAc), dioxane, toluene, xylene, dimethyl sulfoxide (DMSO), dimethyl formamide (DMF), ethyl acetate, methyl ethyl ketone (MEK), and acetonitrile. 1-methyl-2-pyrrolidinone (NMP).

The one or more solvents are selected based on one or more of the one or more biological agents and heparin used for preparing the coating composition. Table 1 illustrates various combinations of the first solvent and the second solvent used for preparing the coating composition in accordance with various embodiments of the invention.

TABLE 1

| First Solvent | Second Solvent |
| --- | --- |
| Acetone | t-butyl alcohol, 1-propanol, 2-propanol, ethanol, carbon tetrachloride, chloroform, cyclohexane, 1,2-dichloroethane, dimethylether, ethyl acetate, and hexane. |
| Dicholoromethane | t-butyl alcohol, 1-propanol, 2-propanol, ethanol, carbon tetrachloride, chloroform, cyclohexane, 1,2-dichloroethane, dimethylether, ethyl acetate, and hexane. |

A particular combination of the first solvent, the second solvent and the one or more of the one or more biological agents and heparin is selected for preparing the coating composition using Table 1. The particular combination is selected based on a desired porosity to be created in the layer. Thereafter, the coating composition is prepared by dissolving a predetermined amount of the one or more of the one or more biological agents and heparin in the mixture of the first solvent and the second solvent. The predetermined amounts of the one or more of the one or more biological agents and heparin are determined based on the desired porosity to be created in the layer. Further, a concentration ratio of the first solvent and the second solvent is also determined based on the desired porosity to be created in the layer. This is illustrated in detail in conjunction with description for Example 1.

Once the coating composition is prepared, the coating composition is applied on the medical device to form the layer. The coating composition may be applied by using one or more of, spray coating, atomization, chemical vapor deposition and similar techniques known in the art. Alternatively, any other suitable method or technique known in the art may be used to apply the coating composition on the medical device to form the layer without departing from the scope of the invention.

The method further includes evaporating at least a part of one of the first solvent and the second solvent present in the layer of the coating composition to create a plurality of pores in the layer at step 104. The evaporation of at least a part of one of the first solvent and the second solvent may be evaporated by subjecting the layer to one or more of an evaporation process, a heat treatment, a vacuum processing, and a fluid flow to evaporate a first solvent of the two or more solvents. Alternatively, one of the first solvent and the second solvent may be evaporated at a room temperature.

In an embodiment, the first solvent has a lower evaporation temperature than the second solvent. In such a scenario, at least a part of the first solvent is evaporated from the layer thereby creating the plurality of pores in the layer. The plurality of pores thus formed may have pores with average diameter ranging from 10 nm to 5000 nm. Alternatively, the plurality of pores may have pores with average diameter ranging from 1 µm to 50 µm.

The average diameter of the pores depends upon one on more factors, such as, but are not limited to, a concentration ratio of the first solvent and the second solvent present in the mixture, the one or more biological agents present in the coating compositions, the first evaporation temperature, the second evaporation temperature, amount of the one or more biological agents present in the coating composition, and the like. Accordingly, the plurality of pores with various desired dimensions may be prepared by varying the one or more factors without departing from the scope of the invention.

Thereafter, the layer with the plurality of pores is allowed to dry. Subsequently, one or more drugs are deposited in the plurality of pores at step 106. The one or more drugs may be deposited in the plurality of pores using one or more of, but are not limited to, spray coating, atomization, chemical vapor deposition and the similar techniques known in the art.

The one or more drugs that may be deposited in the plurality of pores include one or more of, but are not limited to, an anti-proliferative agent, an anti-restenotic agent, an anti-inflammatory agent, an anti-neoplastic agent, an anti-coagulant agent, an anti-fibrin agent, an antithrombotic agent, an anti-mitotic agent, an antibiotic agent, an anti-allergic agent, an antioxidant, an anti-proliferative agent, an estrogen, a protease inhibitor, antibodies, an immunosuppressive agent, a cytostatic agent, a cytotoxic agent, a calcium channel blocker, a phosphodiesterase inhibitor, a prostaglandin inhibitor, a dietary supplement, a vitamin, an anti-platelet aggregating agent and genetically engineered epithelial cells.

Examples of the one or more drugs include, but are not limited to, sirolimus, tacrolimus, paclitaxel, clobetasol, dexamethasone, gestein, heparin, beta-estadiol, rapamycin, everolimus, ethylrapamycin, zotarolimus, ABT-578, Biolimus A9, docetaxel, methotrexate, azathioprine, vincristine, vinblastine, fluorouracil, doxorubicin hydrochloride, mitomycin, sodium heparin, a low molecular weight heparin, a heparinoid, hirudin, argatroban, forskolin, vapiprost, prostacyclin, a prostacyclin analogue, dextran, D-phe-pro-arg-chloromethylketone, dipyridamole, glycoprotein IIb/IIIa, recombinant hirudin, bivalirudin, nifedipine, colchicines, lovastatin, nitroprusside, suramin, a serotonin blocker, a steroid, a thioprotease inhibitor, triazolopyrimidine, a nitric oxide or nitric oxide donor, a super oxide dismutase, a super oxide dismutase mimetic, estradiol, aspirin, angiopeptin, captopril, cilazapril, lisinopril, permirolast potassium, alpha-interferon, bioactive RGD and any salts or analogues thereof.

Further, the one or more drugs may be formulated as one or more of nano-crystals, micro-crystals, nano-carriers, micro-carriers, and any other form suitable for depositing the one or more drugs in the plurality of pores. In an embodiment, the one or more drugs are formulated as nano-crystals. In another embodiment, the one or more drugs are formulated as nano-carriers. The nano-carriers include the nano-crystals of the one or more drugs encapsulated with one or more biological agents. The nano-carriers have an average diameter ranging from 1 nm to 5000 nm. Alternatively, the nano-carriers may have two or more different average diameters.

Thus, a medical device having a layer with the plurality of pores coated on surface of the medical device and the one or more drugs loaded in the plurality of pores is obtained. When such medical device is positioned and expanded at a target site, the one or more drugs are released from the plurality of pores. The medical device may be used to deliver the one or more drugs to a target site for treating one or more medical conditions. The one or more medical conditions may include, but are not limited to, thrombus in a blood vessel, restenosis, acute myocardial infarction, and the similar cardiovascular diseases.

In an embodiment, the medical device is a catheter balloon. The outer surface of the catheter balloon is coated with the coating composition to form the layer. The layer is subsequently subjected to evaporation thereby evaporating at least a portion of one of the first solvent and the second solvent present in the coating composition. Evaporation of the portion of one of the first solvent and the second solvent results in creation of a plurality of pores in the layer. Thereafter, the nano-carriers of the one or more drugs are deposited in the plurality of pores to obtain a catheter balloon loaded with the one or more drugs. When the catheter balloon thus obtained is positioned and inflated at a target site in a body lumen, the plurality of pores is expanded. In response to the expansion of the plurality of pores, the nano-carriers are released from the plurality of pores and the nano-carriers are transferred to the target site.

In another embodiment, the insertable medical device is the pre-crimped stent (a stent mounted on a balloon). An outer surface of the pre-crimped stent is coated with a coating composition to form the layer when the balloon is mounted on the stent. Thus, one or more portions of the balloon that are not covered with the stent and the outer surface of the stent are coated with the layer. The layer is subsequently subjected to evaporation thereby evaporating at least a portion of one of the first solvent and the second solvent present in the coating composition. Evaporation of the portion of the one of the first solvent and the second solvent creates a plurality of pores in the layer that is present on the one or more portions of the balloon and the outer surface of the stent. Thereafter, the nano-carriers of the one or more drugs are deposited in the plurality of pores. Thus, a pre-crimped stent loaded with the nano-carriers on the outer surface of the stent and the one or more portions of the balloon is obtained.

When the pre-crimped stent is positioned and expanded at the target site, the nano-carriers present in the plurality of pores of the layer coated on the one or more portions of the balloon provide burst release of the nano-carriers. Whereas, the nano-carriers present in the plurality of pores of the outer surface of the stent may provide for a delayed release. Further, one or more desired rates of release of the nano-carriers may be achieved by varying average diameters associated with one or more of the plurality of pores and the nano-carriers. The average diameters associated with one or more of the plurality of pores and the nano-carriers may range from 10 nm to 5000 nm.

In yet another embodiment, a solution of one or more polymers is added to the coating composition prepared as described in FIG. 1. In such a scenario, the solution of the one or more polymers is prepared by dissolving the one or more polymers in the mixture of two or more solvents with different evaporation temperatures. Thus, a coating composition containing the one or more polymers and one or more of the one or more biological agents and heparin is obtained. Thereafter, such coating composition is used to coat the medical device as described in FIG. 1 to create a porous layer.

The one or more polymers used to create such porous layer may include, for example, but are not limited to, a homopolymer; a co-polymer of glycolide and lactide; a co-polymer of trimethylene carbonate; e-caprolactone and polydiaxanone; Poly Glycolic Acid (PGA); Poly(Lactic-co-Glycolic Acid) (PLGA); Poly(Ethylene Glycol) (PEG); Polyglactin; Polyglyconate; Polydiaxanone; Polyglecaprone; Polyglycolide; Polylactide; Polyhydroxybutyrate; Poly(Glycolide-E-Caprolactone); Poly(Glycolide Trimethylene Carbonate); Poly(L-lactic Acide-L-lysine) copolymer; Tyrosine-based polyarylates; Polyiminocarbonates; Polycarbonates; Poly(D;L-lactide-Urethane); Poly(esteramide); Poly-P-Dioxanone; hyaluronic acid; chitin; chitosan; Poly-L-Glutamic Acid; Poly-L-Lysine; Polyphosphazene; Poly[bis(carboxylatophenoxy)phosphazene] and any combination thereof. Alternatively, any other biocompatible polymer may be used for creating the polymer layer without departing from the scope of the invention.

Whereas, the two or more solvents present include, for example, but are not limited to, an alcohol, a chlorine substituted methane, a chlorine substituted ethane, an ether, an ester. Examples of the two or more solvents include, but are not limited to, methanol, ethanol, iso-propyl alcohol, trichloromethane, tetrachloromethane, tetrachloroethane, trochloroethane, Dimethyl sulfoxide (DMSO), tricholoethyline, tetrahydrofuran, dichloromethane, chloroform, n-propanol, dimethylformamide, dimethylacetamide. In some embodiments, the one or more solvents include alcohols (e.g., methanol, ethanol, n-propanol, iso-propanol, n-butanol, iso-butanol), heptane, hexane, pentane, cyclohexanone, trichloroethane, acetone, tetrahydrofuran (THF), dimethyl acetamide (DMAc), dioxane, toluene, xylene, dimethyl sulfoxide (DMSO), dimethyl formamide (DMF), ethyl acetate, methyl ethyl ketone (MEK), acetonitrile, and 1-methyl-2-pyrrolidinone (NMP).

In an embodiment, the one or more polymers and one or more of the one or more biological agents and heparin are dissolved in the two or more solvents with different evaporation temperatures to obtain a coating composition. The coating composition thus prepared is then used to create a porous layer on the surface of the medical device as described in FIG. 1.

Pursuant to various embodiments, the invention also provides a medical device prepared in accordance with methods of the invention. The medical device includes one or more of, but are not limited to, an insertable medical device and an implantable medical device. Examples of the medical device include, but are not limited to, a stent, a balloon, a pre-crimped stent, a catheter and an implant. Alternatively, the medical device may be any other medical device that may be inserted or implanted into a body lumen without departing from the scope of the invention. In an embodiment, the medical device is a catheter balloon. In another embodiment, the medical device is a stent. In yet another embodiment, the medical device is a pre-crimped stent.

The medical device includes a surface. The surface of the medical device is coated with a layer including one or more biological agents. The layer further includes a plurality of pores. The plurality of pores have one or more drugs deposited therewithin.

In another embodiment, the medical device includes a layer coated on the surface of the medical device. The layer includes one or more polymers and one or more of the one or more biological agents and heparin. The layer further includes a first plurality of pores. The plurality of pores includes a drug deposited in the plurality of pores.

EXAMPLE 1

Preparation of Coating Compositions in Accordance with Embodiments of the Invention Preparation of coating composition 1: Lipoid E80 was dissolved in 80 ml acetone or dichloromethane to obtain Solution 1. After complete dissolution of Lipoid E80, 20 ml iso-propanol was added to Solution 1. Solution 1 was then shaken well and was stored in an air-tight amber colored Standard Measuring Flask (SMF) as coating composition 1.

Preparation of coating composition 2: Heparin benzalkonium was dissolved in 80 ml acetone or dichloromethane to obtain solution 2. Heparin benzalkonium was dissolved in 20 ml iso-propanol to obtain Heparin benzalkonium solution. The Heparin benzalkonium solution was added to solution 2 to obtain coating composition 2. The coating composition 2 thus obtained was shaken well and was stored under refrigeration in an air-tight amber colored SMF.

Preparation of solution of sirolimus: Sirolimus was dissolved in the acetone to obtain a solution of sirolimus. The solution of sirolimus was then shaken well and stored under refrigeration in an air-tight amber colored SMF.

Preparation of solution of poly glycolic acid (PGA): PGA was dissolved in 80 ml dicholoromethane and 10 to 20 ml of ethyl acetate was added in the resultant solution. The resultant solution of PGA was shaken well and stored.

EXAMPLE 2

Figure 2:
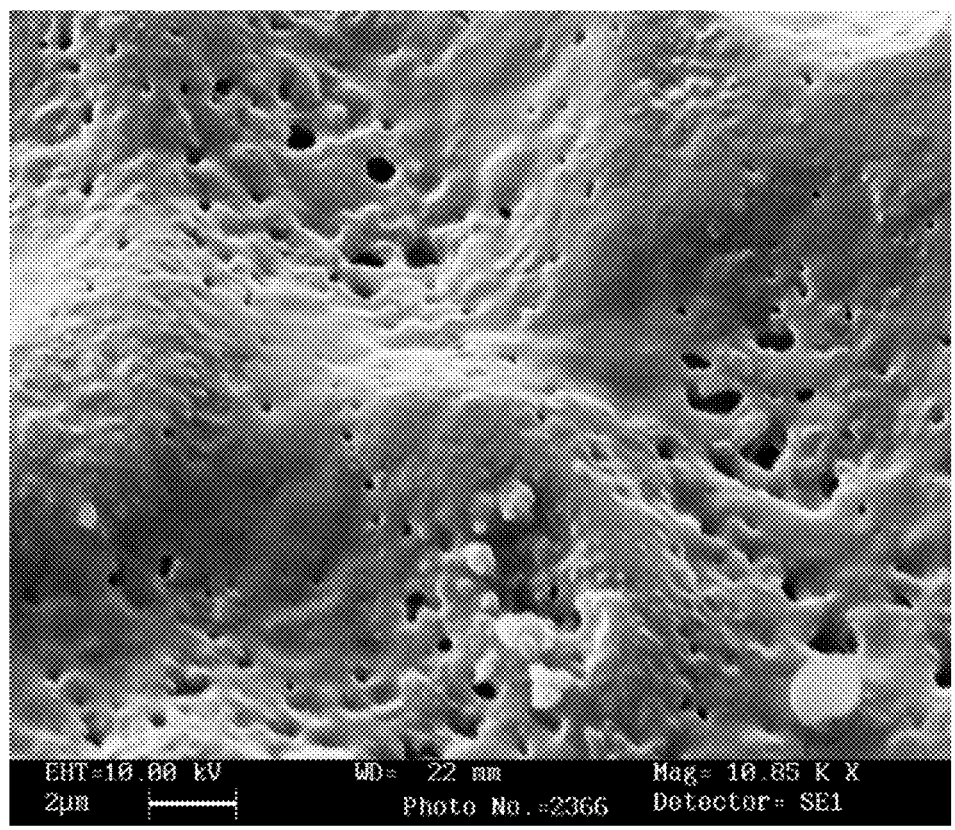
FIG. 2 illustrates a microscopic image of a porous layer created on the surface of catheter system in accordance with Example 2.

Method of Coating a Medical Device with a (Porous) Layer Made Up of Biological Agents Yangtze μ PTCA catheter (hereinafter referred to as "catheter system") was used for coating. The catheter system was mounted on mandrel of a coating machine. 2 ml of coating composition 1 was fed into reservoir of the coating machine. The catheter system was exposed to nozzle of the coating machine and coating composition 1 was sprayed on the catheter system. Room temperature was maintained at 20° C. to control evaporation of acetone or dichloromethane. Thereafter, the catheter system was kept in a vacuum for 1 to 5 hours at 45° C. to 60° C. for porous formation using evaporation of second solvent. Time interval of vacuum, evaporation, and temperature were varied as required. A catheter system coated with a porous layer of Lipoid E80 was thus obtained. Subsequently, the dried catheter system coated with the porous layer of Lipoid E80 was again sprayed with the solution of sirolimus prepared in Example 1 using the coating machine. The catheter system thus sprayed with the solution of sirolimus was allowed to dry under vacuum at 30° C. for 20 minutes. The catheter system thus obtained contained the porous layer of Lipoid E80, wherein crystals of sirolimus are deposited in the pores of the porous layer. FIG. 2 illustrates a high resolution SEM image of a porous layer created on the surface of catheter system in accordance with Example 2.

EXAMPLE 3

Method of Coating a Medical Device with a (Porous) Layer Made Up of Heparin

Yangtze μ PTCA catheter (hereinafter referred to as "catheter system") was used for coating a medical device. The catheter system was mounted on mandrel of a coating machine. 2 ml of coating composition 2 was fed into reservoir of the coating machine. The catheter system was exposed to a nozzle of the coating machine and coating composition 2 was sprayed on the catheter system. Room temperature was maintained at 20° C. to control evaporation of acetone or dichloromethane. Thereafter, the catheter system was kept in a vacuum for 1 to 5 hours at 45° C. to 60° C. for porous formation using evaporation of second solvent. Time interval of the vacuum, evaporation, and temperature were varied as required. A catheter system coated with a porous layer of Heparin benzalkonium was thus obtained. Subsequently, the dried catheter system coated with the porous layer of Heparin benzalkonium was again sprayed with the solution of sirolimus prepared in Example 1 using the coating machine. The catheter system thus sprayed with the solution of sirolimus was allowed to dry under vacuum at 30° C. for 20 minutes. The catheter system thus obtained contained the porous layer of Heparin benzalkonium, wherein crystals of sirolimus was deposited in the pores of the porous layer.

EXAMPLE 4

Method of Coating a Medical Device with a Mixture of Polymer and a Biological Agent Yangtze μ PTCA catheter (hereinafter referred to as "catheter system") was used for coating. Solution 1 and solution of PGA prepared in accordance with example 1, were mixed to obtain a mixture. The catheter system was exposed to a nozzle of a coating machine and the mixture was sprayed on the catheter system. Room temperature was maintained at 20° C. to control evaporation of acetone or dichloromethane. Thereafter, the catheter system was kept in a vacuum for 1 to 5 hours at 45° C. to 60° C. Time interval of vacuum evaporation, and temperature were varied as required. A catheter system coated with a porous layer of Lipoid E80 and polymer (PGA) was thus obtained. Subsequently, the dried catheter system coated with the porous layer of Lipoid E80 was again sprayed with the solution of sirolimus prepared in Example 1 using the coating machine. The catheter system thus sprayed with the solution of sirolimus was allowed to dry under vacuum at 30° C. for 20 minutes. The catheter system thus obtained contained a sirolimus deposited in the porous layer of Lipoid E80 and the polymer.

Various embodiments of the invention provide method for coating a medical device such that a drug is deposited in pores in a layer coated on the medical devices. This facilitates in reducing loss of the drug during transit of the medical device to a target site. Further, the drug may be loaded on the medical device without using a polymer and without modifying the surface of the medical device. Thus, the side effects associated with the use of the polymers for loading the drug on the medical device may be minimized.

Those skilled in the art will realize that the above-recognized advantages and other advantages described herein are merely exemplary and are not meant to be a complete rendering of all of the advantages of the various embodiments of the invention.

In the foregoing specification, specific embodiments of the invention have been described. However, one of ordinary skill in the art appreciates that various modifications and changes can be made to the invention without deviating from the scope of the invention. Accordingly, the specification is to be regarded in an illustrative rather than a restrictive sense, and all such modifications are intended to be included within the scope of the invention.

What is claimed is:

1. A method of coating a medical device, comprising:
    applying a coating composition on an expandable balloon surface of the medical device to form a first layer on the medical device, and applying the coating composition on a stent surface of the medical device to form a second layer on the medical device, the coating composition comprising at least one biological agent and heparin dissolved in a mixture of a first solvent and a second solvent, the first solvent and the second solvent having different evaporation temperatures;
    evaporating at least a part of one of the first solvent and the second solvent present in the coating composition to create a plurality of expandable pores in the first layer and the second layer;
    depositing at least one drug in the plurality of expandable pores, wherein the drug is released in relation to a degree of expansion of the first layer and the second layer possessing the plurality of expandable pores; and
    wherein when the medical device is positioned and expanded at a target site, the plurality of expandable pores of the first layer coated on the expandable balloon surface provide a burst release of the at least one drug, and the plurality of expandable pores of the second layer coated on the stent surface provide a delayed release of the at least one drug.

2. The method of claim 1, wherein the at least one drug is formulated as at least one of nano-crystals, nano-carriers, micro-crystals and micro-carriers.

3. The method of claim 1, wherein the at least one biological agent is selected from at least one of a drug carrier, a blood component, a phospholipid, solid lipid nano-particles, a lipoid, a vitamin and a sugar molecule.

4. The method of claim 1, wherein the at least one biological agent is selected from at least one of a steroid, an estradiol, an esterified fatty acid, a non-esterified fatty acid, glucose, an inositol, L-lactate, a lipoprotein, a carbohydrates, tricalcium phosphate, precipitated calcium phosphate, a substance derived from one of human, egg and soybean, phospholipon 80H, phospholipon 90H, Lipoid S75, Lipoid E80, Intralipid 20, Lipoid EPC, Lipoid E75, a lipid obtained from one of egg and soya, phosphatidylcholine, phosphatidylglycerol, phosphatidylinositol, phosphatidylserine, phosphatidic acid, cardiolipin, and phosphatidylethanolamine.

5. The method of claim 1, wherein at least one of the first solvent and the second solvent is selected from at least one of methanol, ethanol, iso-propyl alcohol, a chloromethane, trichloromethane and tetrachloromethane, dimethylformamide, ethyl acetate, a low boiling ether, and a low boiling ester.

6. The method of claim 1, wherein the medical device is one of a stent, a balloon, a pre-crimped stent, an implant and an insertable medical device.

7. The method of claim 2, wherein the nano-carriers of the at least one drug comprise the at least one drug encapsulated with at least one biological agent.

8. The method of claim 7, wherein the at least one drug is selected from at least one of an anti-proliferative agent, an anti-restenotic agent, an anti-inflammatory agent, an anti-neoplastic agent, an anti-coagulant agent, an anti-fibrin agent, an antithrombotic agent, an anti-mitotic agent, an antibiotic agent, an anti-allergic agent, an antioxidant, an anti-proliferative agent, an estrogen, a protease inhibitor, antibodies, an immunosuppressive agent, a cytostatic agent, a cytotoxic agent, a calcium channel blocker, a phosphodiesterase inhibitor, a prostaglandin inhibitor, a dietary supplement, a vitamin, an anti-platelet aggregating agent and genetically engineered epithelial cells.

9. The method of claim 7, wherein the at least one biological agent is selected from at least one of a drug carrier, a blood component, a phospholipid, solid lipid nano-particles, a lipoid, a lipid, a vitamin and a sugar molecule.

10. The method of claim 7, wherein an average diameter of the nano-carriers of the at least one drug ranges from 10 nm to 1000 nm.

11. The method of claim 1, wherein the coating composition further comprises at least one polymer.

12. The method of claims 11, wherein the at least one polymer is at least one of a homopolymer; a co-polymer of glycolide and lactide; a co-polymer of trimethylene carbonate; e-caprolactone and polydiaxanone; Poly Glycolic Acid (PGA); Poly(Lactic-co-Glycolic Acid) (PLGA); Poly(Ethylene Glycol) (PEG); Polyglactin; Polyglyconate; Polydiaxanone; Polyglecaprone; Polyglycolide; Polylactide; Polyhydroxybutyrate; Poly(Glycolide-E-Caprolactone); Poly(Glycolide Trimethylene Carbonate); Poly(L-lactic Acide-L-lysine) copolymer; Tyrosine-based polyarylates; Polyiminocarbonates; Polycarbonates; Poly(D;L-lactide-Urethane); Poly(esteramide); Poly-P-Dioxanone; hyaluronic acid; chitin; chitosan; Poly-L-Glutamic Acid; Poly-L-Lysine; Polyphosphazene; Poly[bis(carboxylatophenoxy)phosphazene] and combinations thereof.

13. A medical device prepared by the method of claim 11.

14. A medical device prepared by the method of claim 1.

* * * * *